United States Patent [19]
Walker

[11] 3,947,122
[45] Mar. 30, 1976

[54] CUVETTE AND STIRRER FOR OXIMETER
[75] Inventor: Terence Walker, East Aurora, N.Y.
[73] Assignee: American Optical Corporation, Southbridge, Mass.
[22] Filed: Dec. 16, 1974
[21] Appl. No.: 533,401

[52] U.S. Cl. ............... 356/41; 259/122; 356/244; 356/246
[51] Int. Cl.² .................. G01N 33/16; G01N 1/10
[58] Field of Search ......... 356/39, 40, 41, 197, 244, 356/246; 259/107, 108, 118, 122

[56] References Cited
UNITED STATES PATENTS
3,296,922  1/1967  Goldberg ........................... 356/40

*Primary Examiner*—Vincent P. McGraw
*Attorney, Agent, or Firm*—Alan H. Spencer; William C. Nealon; H. R. Berkenstock, Jr.

[57] ABSTRACT

An Oximeter Cuvette having a complimentary cover with a stirrer that extends into the cuvette cavity and which is rotated relative to the cuvette by the oximeter unit is particularly advantageous to permit a plurality of samples to be evaluated rapidly.

8 Claims, 4 Drawing Figures

CUVETTE AND STIRRER FOR OXIMETER

BACKGROUND OF THE INVENTION

This invention relates to oximeter cuvettes and more particularly to an oximeter cuvette having a complimentary cover with a stirrer.

In vitro oximeters such as those disclosed and claimed in U.S. Pat. No. 3,296,922 used an expensive cuvette which is manufactured to extremely close tolerance in combination with a permanent stirring mechanism and cover combination. The permanent stirring mechanism and cover combination is used to position the cuvette and secures the cuvette firmly against the glass plate through which the measurement transmission is passed. In devices of this type, it is necessary to clean the stirring mechanism and cover between the evaluation of each successive sample. Since the cleaning of the cover and stirrer, as well as the cuvette, involves sterilization, a substantial delay is incurred between successive tests, unless the operator has a supply of sterilized covers, stirrers and cuvettes.

BRIEF DESCRIPTION OF THE PRESENT INVENTION AND DRAWINGS

A cylindrical cuvette for an oximeter having a complimentary cover with a stirrer mounted thereon that may be driven by the oximeter is particularly advantageous in that it may be disposed of after a single use.

It is an object of this invention to provide a cuvette for use with a liquid reflectance measuring apparatus and a complimentary cover having a stirrer mounted thereon.

It is another object of the present invention to provide a disposable cuvette and stirrer assembly for use with an oximeter.

It is a still further object of the present invention to provide a disposable cuvette and stirrer assembly for use with an oximeter having an external gear on the cover to engage a drive gear on the oximeter unit.

DETAILED DESCRIPTION OF THE PREFERRED EMBODIMENT

Figure 1:
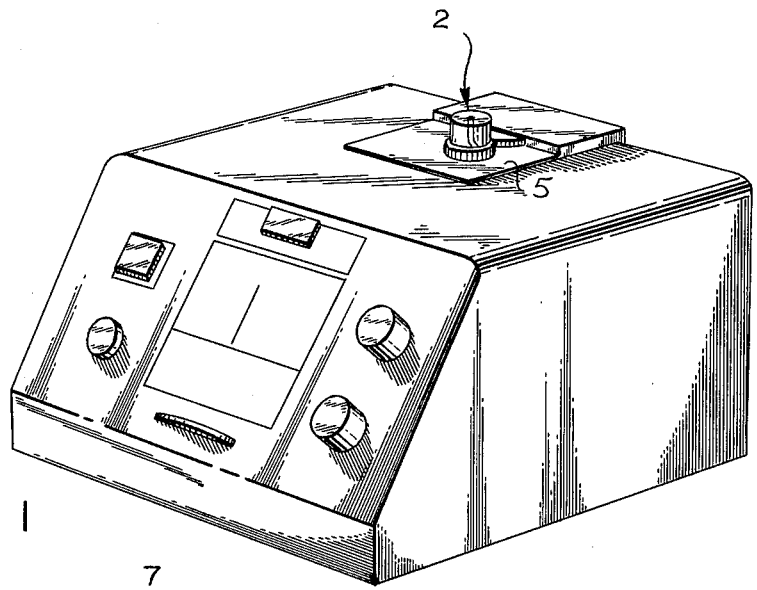
FIG. 1 is a perspective view of an oximeter having the cuvette and cover assembly positioned for evaluation of a blood sample.
Figure 2:
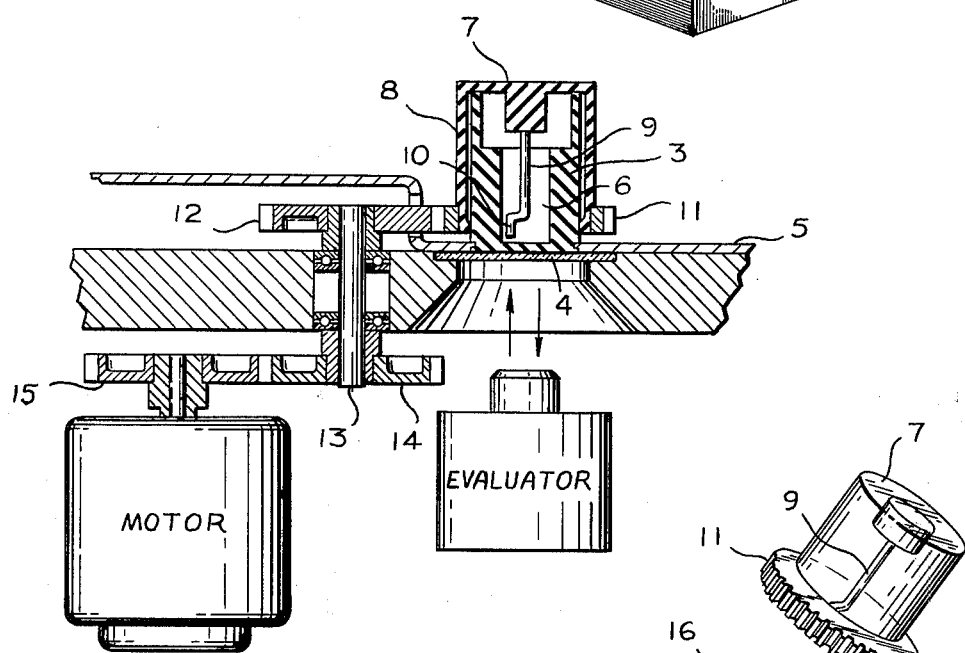
FIG. 2 is a side view partly in section showing the mechanism for driving the stirrer according to one embodiment of the present invention.

FIG. 1 shows an oximeter 1 generally having a cuvette-cover assembly 2 positioned for evaluation of a blood sample (not shown). Referring to FIG. 2, cuvette 3 is firmly secured against glass plate 4 by retainer 5. Glass plate 4 permits light to be transmitted to the blood sample (not shown) from the evaluator and reflected light to be transmitted from the blood sample to the evaluator. Cuvette 3 has a recess 6 acting as the blood chamber and is sealed by cover 7, which has a complimentary sidewall 8 extending toward the base of cuvette 3 and a stirrer 9 mounted coaxially to the cover. Stirrer 9 has an axially displaced portion 10 located within recess 6. External gear 11 is mounted near the base of sidewall 8 and engages drive gear 12. Drive gear 12 is connected to the motor by shaft 13 and intermediate gears 14 and 15. An inwardly extending flange provides a bearing surface 21 to coaxially align cover 7 and cuvette 3 with minimum friction while maintaining engagement of external gear 11 and drive gear 12.

Figure 3:
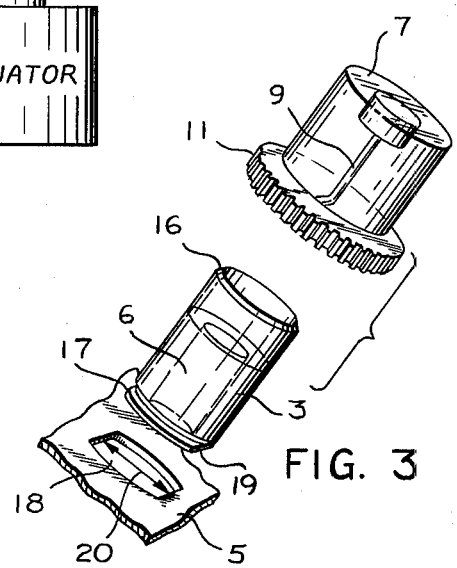
FIG. 3 is a perspective view showing, in spatial relationship, the cover, cuvette, and plate for positioning the cuvette.

IN FIG. 3, cover 7 with stirrer 9 and external gear 11 is shown in a spatial relationship to cuvette 3 and retainer 5. In operation, cover 7 rests on top edge 16 which is preferrably tapered to reduce resistance of the relative rotary motion between cover 7 and cuvette 3. The bottom end of cuvette 3 has a pair of diametrically opposed flange sections 17 (one shown). Retainer 5 has opening 18 which is shaped complimentary to the cross-section of the bottom 19 of cuvette 3. The cuvette is inserted through opening 18 and rotated until flange sections 17 are under edges 20 of retainer 5. In this position, cuvette 3 is seated firmly against plate 4 and the frictional engagement between flange sections 17, retainer 5 and glass plate 4 prevents rotation of cuvette 3 when the motor is started and cover 7 is rotated thereby.

Figure 4:
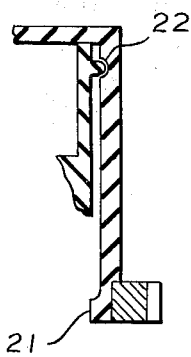
FIG. 4 is a partial cross-section of another embodiment of the cuvette and cover.

FIG. 4 shows another embodiment in which cover 7 has radial groove 22 extending around the interior of sidewall 8 and cuvette 3 has a complimentary external flange 23 which snaps into groove 22 to prevent unintentional axial displacement of cover 7 during rotation.

What is claimed is:

1. A cuvette and stirrer assembly for use with liquid reflectance measuring apparatus having a drive gear which comprises a cuvette including a circular cross-sectioned, cylindrical body having a cylindrical coaxial recess in the top thereof to hold a liquid sample, the bottom of said body being transparent and having a planar exterior surface adapted to transmit light from said apparatus into said recess, and a stirrer including a hollow cover having a cylindrical cavity in one end thereof and complimentary to the exterior of said body, said cavity being adapted to receive said body and to align said cavity and said recess coaxially, the other end of said cover being a top, said top having an elongated member extending therefrom into said recess, a portion of said elongated member being located within said recess and being spaced from the axis thereof, an external gear concentrically mounted on said cover to engage the drive gear whereby said cover may be rotated relative to said body and said sample stirred by the member during measuring.

2. The assembly according to claim 1 wherein said gear is mounted adjacent said one end of cover.

3. The assembly according to claim 1 wherein the bottom of said recess and the bottom of the body are parallel planes.

4. The assembly according to claim 1 wherein the top of the cavity rests on the top of the body to support said hollow cover.

5. The assembly according to claim 1 wherein the member extends coaxially from said cover to said portion of said member.

6. The assembly according to claim 1 further including means to prevent relative axial motion between said cuvette and said cover without restricting relative rotation therebetween.

7. A cuvette stirrer assembly for use with an in vitro reflectance oximeter having means to temporarily hold and prevent rotation of the cuvette and a drive gear which comprises a cuvette body including a circular cross-sectioned, cylindrical recess in the top thereof to hold a blood sample, the bottom of said cuvette having a planar exterior surface adapted to transmit light from said oximeter into said recess and to transmit light reflected from the blood sample back into the oximeter, a circumferential groove and an irregular area in the exterior surface adjacent the bottom of said body cooperating with said means to temporarily hold and prevent rotation of the cuvette, and a stirrer including a hollow cover having a cylindrical cavity in one end thereof complimentary to the exterior of said body, said cavity being adapted to receive the top of said body and to align said cavity and said recess coaxially, the other end of said cover being adapted to support said cover by resting on the top of said body, an elongated member extending coaxially from said top into said recess, a portion of said member being within said recess and being spaced from the axis thereof, an external gear concentrically mounted said one end of said cover to engage the drive gear, whereby said cover may be rotated relative to the cuvette and the blood sample is stirred by the member during reflectance oximetry determinations.

8. In combination, a reflectance oximeter for determining the percentage of oxygen saturation in whole blood and the cuvette and stirrer assembly of claim 7.

* * * * *